Figure 1:
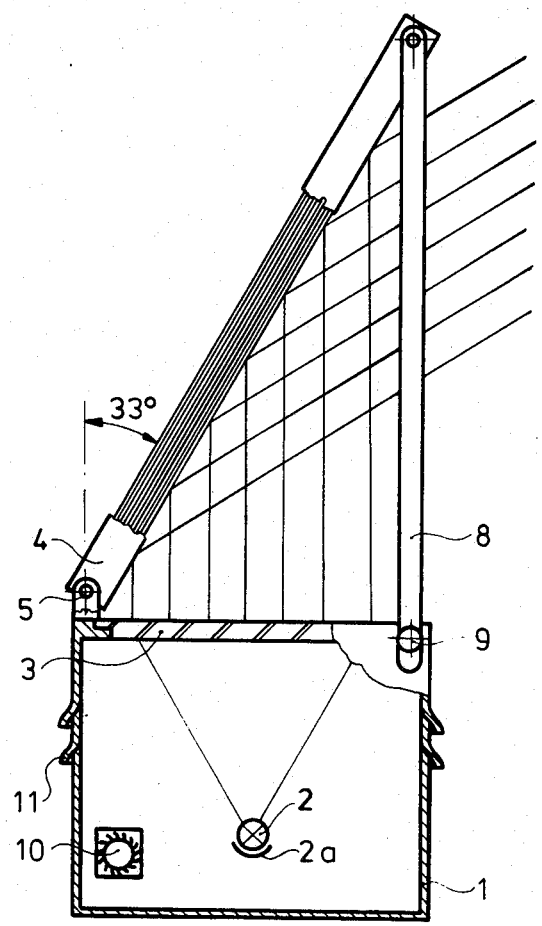

United States Patent [19]

Schlyter

[11] Patent Number: 4,612,604
[45] Date of Patent: Sep. 16, 1986

[54] PROJECTOR FOR PRODUCING A LIGHT SPOT OF POLARIZED LIGHT FOR BIOSTIMULATION PURPOSES

[75] Inventor: Yngve S. G. Schlyter, Malmoe, Sweden

[73] Assignee: Bildsystem AB, Malmo, Sweden

[21] Appl. No.: 683,007

[22] Filed: Dec. 18, 1984

[30] Foreign Application Priority Data

Dec. 23, 1983 [SE] Sweden .............................. 8307157

[51] Int. Cl.⁴ ................................................ F21V 9/14
[52] U.S. Cl. ..................................... 362/19; 362/328; 362/373
[58] Field of Search ................. 362/19, 263, 264, 277, 362/278, 293, 294, 296, 307, 308, 327, 328, 329, 373; 353/66

[56] References Cited

U.S. PATENT DOCUMENTS

| | | | |
|---|---|---|---|
| 2,028,505 | 1/1936 | Eitzen | 362/277 X |
| 2,098,990 | 11/1937 | Newton | 362/277 X |
| 3,162,378 | 12/1964 | Zillmer | 362/373 X |
| 3,342,101 | 9/1967 | Zollner | 353/66 X |
| 3,457,400 | 7/1969 | Appleldorn | 362/307 X |
| 3,473,013 | 10/1969 | Rogers | 362/19 |
| 3,665,179 | 5/1972 | McLintic | 362/293 |
| 3,762,809 | 10/1973 | Kato et al. | 353/66 |
| 3,876,285 | 4/1975 | Schwarzmuller | 362/19 X |
| 3,912,920 | 10/1975 | Kubota | 362/19 |
| 4,428,031 | 1/1984 | Mori | 362/277 X |

FOREIGN PATENT DOCUMENTS 1521715 8/1978 United Kingdom .
2105195 3/1983 United Kingdom .

Primary Examiner—W. R. Wolfe
Attorney, Agent, or Firm—Merchant, Gould, Smith, Edell, Welter & Schmidt

[57] ABSTRACT

A uniform beam of polarized light for biostimulation purposes is provided by a projector having a lamp, and a reflector which create a diverging beam that refracts through a Fresnel lens and becomes a bundle of parallel beams, which strikes a multi-plate Brewster polarizer to be reflected and become a polarized light bundle of substantially parallel light beams of nearly uniform intensity and having a dimension of some hundreds of cm². The projector may include a rectangular housing, a pair of rods hingedly connecting a frame around the polarizer and engaging the housing to position the polarizer, a halogen overhead projector lamp, a cooling fan and a six plate glass polarizer.

16 Claims, 2 Drawing Figures

PROJECTOR FOR PRODUCING A LIGHT SPOT OF POLARIZED LIGHT FOR BIOSTIMULATION PURPOSES

The invention relates to a projector for producing a light spot of polarised light for biostimulation purposes.

BACKGROUND OF THE INVENTION

Recent discoveries have shown that the application of polarised light of higher intensities can have a beneficial effect on wound-healing and in a large number of other medical and/or cosmetic applications. The biostimulation effect attributed to the polarised light can also be utilised for certain industrial purposes.

GB No. 2,105,195 (DE No. 3220218.0) discloses the basic theory of biostimulation and a number of lamp arrangements capable of generating polarised light. These lamp arrangements generally comprise a halogen bulb, a reflector, a light collimating system and a polariser. The parallel bundle of light is provided either by a lens system or by a long tube preventing the passage of diverging light. In addition to the cooling problems connected with these arrangements, the maximum spot area cannot exceed a few tens of cm². The divergence of the beams makes it necessary to place the lamp arrangement at a distance of about 20–30 cm from the surface to be treated.

In practical applications, the areas to be treated are often larger than the spot area, and therefore scanning of the lamp arrangement is required to provide full illumination of the wound area. The need for scanning implies a number of drawbacks and can be the source of subjective errors caused by uneven scanning movements. In certain applications, a larger lamp-to-surface distance would be preferable.

OBJECT OF THE INVENTION

The object of the present invention is to provide an improved polarised light source which is capable of uniformly illuminating larger areas from greater distances.

SUMMARY OF THE INVENTION

This object is attained according to the present invention by the combination of a high power lamp in a housing with a Fresnel lens which is capable of collimating the diverging light beams in a large parallel bundle, and a Brewster polariser arranged in the path of the parallel beams.

The Fresnel lens has a larger transparency than an optical lens system with the same optical performance. Moreover, it weighs far less and also is less complicated in design.

In general, the light source according to the invention can be designed similar to an overhead projector in which the Brewster polariser can be arranged in a frame hingedly connected to the upper rear portion of the housing.

The projector according to the invention can be used at a distance of 1.5–3 m from the surface to be treated, which is much more convenient than the presently available distances of 0.2–0.3 m. The full spot area can be as large as 500–700 cm², which generally is sufficient to eliminate the need for separate scanning.

BRIEF DESCRIPTION OF THE DRAWING AND A PREFERRED EMBODIMENT

Figure 2:
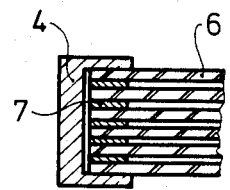

The invention will now be described by means of a preferred embodiment, reference being made to the accompanying drawing in which:

FIG. 1 is a schematic elevational view, partly in section, of the projector according to the invention; and FIG. 2 shows an enlarged detail of the frame with the glass plates.

The projector shown in the drawing comprises a box-like housing 1 in which a metal halogen lamp 2 is arranged. The lamp 2 has a power of several hundreds of watts and is typically an overhead projector lamp, such as Philips type 7804 with a power of 900 W. A reflector 2a is built together with the lamp 2 to reflect the downward light beams towards the top portion of the housing 1 which defines a large rectangular opening. The reflector 2a is designed to reflect the light beams upwards with a divergence as indicated in FIG. 1 to provide an even distribution through the opening. A Fresnel lens 3 is mounted in the opening in such a way that it substantially seals the inner part of the housing 1. The Fresnel lens 3 is designed to form the diverging incident beams of the lamp 2 into a parallel bundle. For this reason, the distance between the plane of the Fresnel lens 3 and the lamp 2 is substantially equal to the focal length of the Fresnel lens 3 which is typically 8.5 inches.

The Fresnel lens 3 which can be used for the present invention is commercially available, for instance from Edmund Scientific Co., Barrington, N.J., U.S.A. and can be of the type K 60,826 or K 71,315.

A frame 4 is mounted on the housing 1 at the upper rear edge thereof by means of a hinge 5. The frame 4 can be folded down on the Fresnel lens 3 to facilitate transportation. A Brewster polariser comprising a number of spaced glass plates 6 is supported by the frame 4. The plane of the glass plates 6 encloses a Brewster angle (57°) with the parallel light beams passing through the Fresnel lens 3. The position of the frame 4 is defined by a pair of supporting rods 8 mounted pivotally on the front portions of the frame 4. The lower end portions of the supporting rods 8 releasably engage locking pins 9 attached to the side walls of the housing 1.

FIG. 2 shows a portion of the frame 4 with the glass plates 6. The spacing between the glass plates 6 is maintained by appropriate resilient spacer members 7. The rear surface of the uppermost glass plate 6 is covered by a non-transparent layer, or a further non-transparent sheet is arranged in the frame 4 to prevent light from passing through. Typically, six glass plates 6 of 2 mm are used, with a spacing of 0.2–1 mm.

In the operating position, the parallel collimated light beams will be reflected both from the front and rear surfaces of each glass plate 6, and a parallel bundle of polarised light will be obtained which has but a small divergence. The cross-sectional area of the bundle is defined by the shape of the opening and of the Fresnel lens 3, and in a typical case the size of the light spot at a distance of 2 m from the Brewster polariser can be 267×267 mm or 203×254 mm. The intensity of the light spot is substantially constant.

In order to prevent the Fresnel lens 3 from being overheated by the lamp 2, air cooling is provided by a radial fan 10. Air circulation is facilitated by appropriate cooling slots 11 in the walls of the housing 1.

The actual construction of the housing 1 with the lamp 2 and the fan 10 can be similar to that of overhead projectors manufactured on a large scale. The Fresnel lens 3, however, is not similar to the lenses used in the overhead projectors because, in such applications, diverging and not parallel light is required.

The projector according to the invention is very simple in design and can provide a highly uniformly illuminated light spot at a remote location. The spot area generally is sufficiently large, and no separate scanning is required for irradiating larger wounds. The large illuminated area facilitates the application of the present projector not only to medical and/or cosmetic uses but also to industrial biostimulation.

The projector can be attached to a bracket not shown in the drawing, whereby any projecting direction can be set and fixed.

What I claim and desire to secure by Letters Patent is:

1. A projector for producing a light spot of polarised light for biostimulation purposes comprising: a lamp, a reflector associated with and arranged behind the lamp for reflecting the light beams in a forward direction and a Brewster polariser arranged in the beam path of the lamp, said reflector arranged behind said lamp to provide diverging forward beams, said lamp is a halogen lamp having a power in the range of several hundred watts, with a Fresnel lens inserted in the path between the Brewster polariser and the lamp so that the lamp lies substantially in the focal zone of the Fresnel lens, whereby the diverging forward beams of the lamp form a bundle of parallel beams impinging the Brewster polariser, in which the cross-sectional area of the reflected parallel polarised light bundle is on the order of some hundreds of cm$^2$ and is reflected at an angle with respect to said forward beams, a rectangular housing surrounding and locating the lamp, said housing defines an opening in the top wall, and said Fresnel lens is attached to said housing to cover the opening, said Brewster polariser including a number of spaced parallel glass plates fixed in a rectangular frame, said frame hingedly connected to a rear upper edge portion of said housing, said frame including supporting rods pivoted at their upper ends to said frame and being releasably engageable with said housing, said rods having a length which ensures that the angular position of said plates relative to said parallel beams corresponds to the Brewster angle.

2. The projector as claimed in claim 1, further comprising: position setting means coupled to said housing for desired setting and fixing of the polarised parallel beams reflected from the Brewster polariser.

3. The projector as claimed in claim 1, wherein the rear surface of the uppermost glass plate of said Brewster polariser is covered by a non-transparent layer.

4. The projector as claimed in claim 1, further comprising: a fan arranged in said housing to provide air-cooling for said lamp.

5. The projector as claimed in claim 4, further comprising: cooling slots positioned in the sides of said housing.

6. The projector as claimed in claim 1, wherein said Brewster polariser includes six plates spaced apart by resilient spacer members.

7. The projector as claimed in claim 6, wherein said plates are spaced apart within the range of 0.2 to 1.0 mm.

8. A projector for producing a light spot of polarized light for biostimulation purposes, comprising:
   a lamp with a power of several hundred watts;
   a reflector arranged closely behind said lamp for reflecting backwardly projected light beams of said lamp in a forward direction, said reflector being shaped for producing diverging reflected light beams with an axis of divergence extending in said forward direction;
   a Fresnel lens spaced from said lamp in said forward direction, said lens having an optical axis coinciding with said axis of divergence, the spacing between said lens and said lamp is substantially equal to the focal distance of said lens, said lens being the type for producing parallel light beams from said reflected beams and from direct beams of said lamp incident thereon;
   a housing around said lamp and said reflector supporting said lens and providing a mounting support for said lamp and said reflector;
   a Brewster type polarizer comprising a number of spaced parallel transparent sheets arranged in the path of said parallel beams, the plane of said sheets closing Brewster's angle with said path, said polarizer being fixed to said housing, said polarizer comprising a substantially non-transparent shield arranged to prevent the passage of light along the optical axis of said lens through the assembly of said sheets, whereby a bundle of substantially parallel beams of linearly polarized light is reflected at an angle with respect to said forward direction from said polarizer and has a cross-sectional area on the order of some hundred of cm$^2$.

9. The projector as claimed in claim 8, wherein said housing has a rectangular form and defines an opening in the top wall, said lens attached to said housing to cover said opening.

10. The projector as claimed in claim 8, wherein said lamp is an overhead projector halogen lamp.

11. The projector as claimed in claim 10 further comprising: a fan arranged in said housing to provide air-cooling for said lamp.

12. The projector as claimed in claim 8, wherein said sheets are made of glass.

13. The projector as claimed in claim 12, wherein said spacing between said sheets is between about 0.2 to 1 mm.

14. The projector as claimed in claim 12 wherein said sheets are six in number.

15. The projector as claimed in claim 12, wherein said polarizer comprises a mounting frame of non-transparent material encircling the edge zones of said sheets, resilient spacing members between said sheets in said edge zones, and said frame hingedly connected to a rear upper edge portion of said housing.

16. The projector as claimed in claim 15, further comprising: supporting rods pivoted at their upper ends to said frame and being releasably engageable with said housing, said rods having a length which ensures that the angular position of said plates relative to said parallel beams corresponds to the Brewster angle.

* * * * *